US012551689B2

(12) United States Patent
Bourquin et al.

(10) Patent No.: US 12,551,689 B2
(45) Date of Patent: Feb. 17, 2026

(54) APPARATUS AND METHODS FOR COUPLING A BLOOD PUMP TO THE HEART

(71) Applicant: CorWave SA, Clichy (FR)

(72) Inventors: Amelie Bourquin, Paris (FR); Antoine Rabardel, Paris (FR); Antoine Rudelle, Versalles (FR); Pierre-Yves Quelenn, Asnieres-sur-Seine (FR)

(73) Assignee: CorWave SA, Clichy (FR)

( * ) Notice: Subject to any disclaimer, the term of this patent is extended or adjusted under 35 U.S.C. 154(b) by 602 days.

(21) Appl. No.: 17/299,749

(22) PCT Filed: Nov. 26, 2019

(86) PCT No.: PCT/IB2019/060144
§ 371 (c)(1),
(2) Date: Jun. 3, 2021

(87) PCT Pub. No.: WO2020/115607
PCT Pub. Date: Jun. 11, 2020

(65) Prior Publication Data

US 2022/0016412 A1 Jan. 20, 2022

Related U.S. Application Data

(60) Provisional application No. 62/775,888, filed on Dec. 5, 2018.

(51) Int. Cl.
*A61M 60/863* (2021.01)
*A61M 60/178* (2021.01)
(Continued)

(52) U.S. Cl.
CPC ........ *A61M 60/863* (2021.01); *A61M 60/178* (2021.01); *A61M 60/216* (2021.01); *A61M 60/81* (2021.01)

(58) Field of Classification Search
CPC .......................... A61M 60/863; A61M 60/178
See application file for complete search history.

(56) References Cited

U.S. PATENT DOCUMENTS 2,842,067 A 7/1958 John et al.
3,107,630 A 10/1963 Johnson et al.
(Continued)

FOREIGN PATENT DOCUMENTS

AU 2013203301 A1 5/2013
AU 2013302455 A1 2/2015
(Continued)

OTHER PUBLICATIONS

U.S. Appl. No. 15/484,101 / U.S. Pat. No. 9,968,720, filed Apr. 10, 2017 / May 15, 2018.
(Continued)

*Primary Examiner* — Carl H Layno
*Assistant Examiner* — Maria Catherine Anthony
(74) *Attorney, Agent, or Firm* — Greenberg Traurig, LLP; Christopher C. Bolten; Robert D. Ward

(57) ABSTRACT

An apparatus for coupling a blood pump to a patients heart is provided. The apparatus includes a sewing ring designed to be sutured to the patients heart, wherein the sewing ring has an opening sized and shaped to receive an inflow cannula of the blood pump. The apparatus further includes a locking element coupled to a housing of the blood pump and transitionable between a closed state and an open state. The locking element is structured to receive the sewing ring in the open state and engage the sewing ring in the closed state to prevent translational and rotational movement of the locking element relative to the sewing ring. In addition, the apparatus includes a biased structure designed to bias the locking element in the closed state.

9 Claims, 12 Drawing Sheets

(51) Int. Cl.

| | |
|---|---|
| *A61M 60/216* | (2021.01) |
| *A61M 60/81* | (2021.01) |

(56) References Cited

U.S. PATENT DOCUMENTS

| | | | |
|---|---|---|---|
| 3,165,061 | A | 1/1965 | Smith et al. |
| 3,608,088 | A | 9/1971 | Dorman et al. |
| 3,620,651 | A | 11/1971 | Peter |
| 3,743,446 | A | 7/1973 | Mandroian |
| 3,765,175 | A | 10/1973 | Ohnaka |
| 4,063,826 | A | 12/1977 | Riepe |
| 4,277,706 | A | 7/1981 | Isaacson |
| 4,384,830 | A | 5/1983 | Wakelin |
| 4,484,095 | A | 11/1984 | Neumann |
| 4,488,854 | A | 12/1984 | Miller |
| 4,498,851 | A | 2/1985 | Kolm et al. |
| 4,648,807 | A | 3/1987 | Tippetts et al. |
| 4,753,221 | A | 6/1988 | Kensey et al. |
| 4,906,229 | A | 3/1990 | Wampler |
| 4,918,383 | A | 4/1990 | Huff et al. |
| 4,931,036 | A | 6/1990 | Kanai et al. |
| 4,939,405 | A | 7/1990 | Okuyama et al. |
| 4,955,856 | A | 9/1990 | Phillips |
| 4,995,857 | A | 2/1991 | Arnold |
| 5,147,388 | A | 9/1992 | Yamazaki |
| 5,263,978 | A | 11/1993 | Kaufmann et al. |
| 5,275,580 | A | 1/1994 | Yamazaki |
| 5,300,111 | A | 4/1994 | Panton et al. |
| 5,360,445 | A | 11/1994 | Goldowsky |
| 5,370,509 | A | 12/1994 | Golding et al. |
| 5,525,041 | A | 6/1996 | Deak |
| 5,588,812 | A | 12/1996 | Taylor et al. |
| 5,840,070 | A | 11/1998 | Wampler |
| 5,924,975 | A | 7/1999 | Goldowsky |
| 5,982,801 | A | 11/1999 | Deak |
| 6,030,336 | A | 2/2000 | Franchi |
| 6,058,593 | A | 5/2000 | Siess |
| 6,079,214 | A | 6/2000 | Bishop |
| 6,083,260 | A | 7/2000 | Aboul-Hosn |
| 6,116,862 | A | 9/2000 | Rau et al. |
| 6,123,725 | A | 9/2000 | Aboul-Hosn |
| 6,176,822 | B1 | 1/2001 | Nix et al. |
| 6,176,848 | B1 | 1/2001 | Rau et al. |
| 6,346,071 | B1 | 2/2002 | Mussivand |
| 6,361,284 | B2 | 3/2002 | Drevet |
| 6,395,026 | B1 | 5/2002 | Aboul-Hosn et al. |
| 6,530,876 | B1 | 3/2003 | Spence |
| 6,532,964 | B2 | 3/2003 | Aboul-Hosn et al. |
| 6,658,740 | B2 | 12/2003 | Habben |
| 6,659,740 | B2 | 12/2003 | Drevet |
| 6,672,847 | B2 | 1/2004 | Dooley |
| 6,723,039 | B2 | 4/2004 | French et al. |
| 6,726,648 | B2 | 4/2004 | Kaplon et al. |
| 6,732,501 | B2 | 5/2004 | Yu et al. |
| 6,811,381 | B2 | 11/2004 | Dooley |
| 6,848,001 | B1 | 1/2005 | Sakamoto et al. |
| 6,935,344 | B1 | 8/2005 | Aboul-Hosn et al. |
| 6,976,996 | B1 | 12/2005 | Aboul-Hosn |
| 7,011,620 | B1 | 3/2006 | Siess |
| 7,027,875 | B2 | 4/2006 | Siess et al. |
| 7,182,727 | B2 | 2/2007 | Aboul-Hosn |
| 7,323,961 | B2 | 1/2008 | Drevet |
| 7,520,850 | B2 | 4/2009 | Brockway |
| 7,696,634 | B2 | 4/2010 | Filardo |
| 7,736,296 | B2 | 6/2010 | Siess et al. |
| 7,839,007 | B2 | 11/2010 | Filardo |
| 7,863,768 | B2 | 1/2011 | Filardo |
| 7,889,877 | B2 | 2/2011 | Lutz |
| 7,988,728 | B2 | 8/2011 | Ayre |
| 8,012,079 | B2 | 9/2011 | Delgado, III |
| 8,152,845 | B2 | 4/2012 | Bourque |
| 8,157,720 | B2 | 4/2012 | Marseille et al. |
| 8,167,593 | B2 | 5/2012 | Gohean et al. |
| 8,333,686 | B2 | 12/2012 | Marseille et al. |
| 8,343,029 | B2 | 1/2013 | Farnan et al. |
| 8,366,401 | B2 | 2/2013 | Pate et al. |
| 8,394,009 | B2 | 3/2013 | Bolyard et al. |
| 8,394,010 | B2 | 3/2013 | Farnan |
| 8,432,057 | B2 | 4/2013 | Filardo |
| 8,449,444 | B2 | 5/2013 | Poirier |
| 8,465,410 | B2 | 6/2013 | Marseille et al. |
| 8,512,012 | B2 | 8/2013 | Akdis et al. |
| 8,550,975 | B2 | 10/2013 | Foster |
| 8,556,795 | B2 | 10/2013 | Bolyard et al. |
| 8,562,508 | B2 | 10/2013 | Dague et al. |
| 8,585,571 | B2 | 11/2013 | Bachman et al. |
| 8,597,350 | B2 | 12/2013 | Rudser et al. |
| 8,610,304 | B2 | 12/2013 | Filardo |
| 8,714,944 | B2 | 5/2014 | Drevet |
| 8,753,256 | B2 | 6/2014 | Bolyard et al. |
| 8,784,291 | B2 | 7/2014 | Farnan et al. |
| 8,821,366 | B2 | 9/2014 | Farnan et al. |
| 8,821,527 | B2 | 9/2014 | Farnan et al. |
| 8,827,888 | B2 | 9/2014 | Bolyard et al. |
| 8,834,136 | B2 | 9/2014 | Drevet |
| 8,852,072 | B2 | 10/2014 | LaRose et al. |
| 8,870,739 | B2 | 10/2014 | LaRose et al. |
| 8,956,275 | B2 | 2/2015 | Bolyard et al. |
| 8,976,546 | B2 | 3/2015 | Wang et al. |
| 9,022,916 | B2 | 5/2015 | Farnan et al. |
| 9,080,564 | B2 | 7/2015 | Drevet |
| 9,089,635 | B2 | 7/2015 | Reichenbach et al. |
| 9,144,669 | B2 | 9/2015 | Wieselthaler |
| 9,145,875 | B2 | 9/2015 | Filardo |
| 9,173,984 | B2 | 11/2015 | LaRose et al. |
| 9,211,367 | B2 | 12/2015 | Farnan et al. |
| 9,308,304 | B2 | 4/2016 | Peters et al. |
| 9,446,180 | B2 | 9/2016 | Vadala, Jr. et al. |
| 9,526,819 | B2 | 12/2016 | Chen |
| 9,572,915 | B2 | 2/2017 | Heuring et al. |
| 9,579,437 | B2 | 2/2017 | LaRose et al. |
| 9,616,158 | B2 | 4/2017 | Yaghdjian |
| 9,694,123 | B2 | 7/2017 | Bourque et al. |
| 9,731,057 | B2 | 8/2017 | Garrigue |
| 9,744,279 | B2 | 8/2017 | Tamez et al. |
| 9,786,150 | B2 | 10/2017 | Kimball et al. |
| 9,861,728 | B2 | 1/2018 | Farnan et al. |
| 9,907,892 | B2 | 3/2018 | Broen et al. |
| 9,956,333 | B2 | 5/2018 | LaRose et al. |
| 9,968,720 | B2 | 5/2018 | Botterbusch et al. |
| 10,166,319 | B2 | 1/2019 | Botterbusch et al. |
| 10,188,779 | B1 | 1/2019 | Polverelli et al. |
| 10,398,821 | B2 | 9/2019 | Botterbusch et al. |
| 10,799,625 | B2 | 10/2020 | Scheffler et al. |
| 10,933,181 | B2 | 3/2021 | Le Duc De Lillers et al. |
| 11,097,091 | B2 | 8/2021 | Botterbusch et al. |
| 11,191,946 | B2 | 12/2021 | Snyder et al. |
| 11,298,522 | B2 | 4/2022 | Botterbusch et al. |
| 11,446,480 | B2 | 9/2022 | Polverelli et al. |
| 11,512,689 | B2 | 11/2022 | Drevet et al. |
| 11,623,077 | B2 | 4/2023 | Le Duc De Lillers et al. |
| 11,712,554 | B2 | 8/2023 | Botterbusch et al. |
| 12,214,182 | B2 | 2/2025 | Polverelli et al. |
| 12,251,550 | B2 | 3/2025 | Quelenn et al. |
| 12,257,427 | B2 | 3/2025 | Snyder et al. |
| 2001/0001278 | A1 | 5/2001 | Drevet |
| 2002/0095210 | A1 | 7/2002 | Finnegan et al. |
| 2002/0146333 | A1 | 10/2002 | Drevet |
| 2002/0165426 | A1 | 11/2002 | Sporer et al. |
| 2003/0002325 | A1 | 1/2003 | Alvandpour et al. |
| 2004/0002624 | A1 | 1/2004 | Yu et al. |
| 2004/0068220 | A1 | 4/2004 | Couvillon et al. |
| 2005/0031474 | A1 | 2/2005 | Zackl |
| 2005/0261543 | A1 | 11/2005 | Abe et al. |
| 2005/0288543 | A1 | 12/2005 | Stenberg et al. |
| 2006/0014999 | A1 | 1/2006 | Heilman et al. |
| 2006/0155158 | A1 | 7/2006 | Aboul-Hosn |
| 2006/0288543 | A1 | 12/2006 | Lubera et al. |
| 2007/0299297 | A1 | 12/2007 | Jarvik |
| 2008/0232987 | A1 | 9/2008 | Drevet |
| 2009/0082778 | A1 | 3/2009 | Beane et al. |
| 2010/0234941 | A1 | 9/2010 | Finocchiaro et al. |
| 2010/0241223 | A1 | 9/2010 | Lee et al. |
| 2010/0268333 | A1 | 10/2010 | Gohean et al. |

(56) References Cited

U.S. PATENT DOCUMENTS

| | | | |
|---|---|---|---|
| 2011/0124950 A1 | 5/2011 | Foster | |
| 2011/0176945 A1 | 7/2011 | Drevet | |
| 2011/0176946 A1 | 7/2011 | Drevet | |
| 2011/0218385 A1 | 9/2011 | Bolyard et al. | |
| 2011/0238172 A1 | 9/2011 | Akdis | |
| 2011/0260449 A1 | 10/2011 | Pokorney | |
| 2012/0035411 A1* | 2/2012 | LaRose | F04D 13/0633 600/16 |
| 2012/0089225 A1 | 4/2012 | Akkerman et al. | |
| 2012/0130153 A1 | 5/2012 | Bolyard et al. | |
| 2012/0177506 A1 | 7/2012 | Örter | |
| 2012/0220816 A1 | 8/2012 | Peters et al. | |
| 2012/0226350 A1 | 9/2012 | Rudser et al. | |
| 2012/0323318 A1 | 12/2012 | Yusuf et al. | |
| 2013/0042753 A1 | 2/2013 | Becker et al. | |
| 2013/0078122 A1 | 3/2013 | Drevet | |
| 2013/0178694 A1 | 7/2013 | Jeffery et al. | |
| 2013/0267779 A1 | 10/2013 | Woolford et al. | |
| 2013/0314047 A1 | 11/2013 | Eagle et al. | |
| 2014/0023533 A1 | 1/2014 | Ishii et al. | |
| 2014/0067057 A1 | 3/2014 | Callaway et al. | |
| 2014/0187852 A1 | 7/2014 | Peters et al. | |
| 2014/0207232 A1 | 7/2014 | Garrigue | |
| 2014/0275723 A1 | 9/2014 | Fritz, IV et al. | |
| 2014/0277423 A1 | 9/2014 | Alkhatib et al. | |
| 2014/0303426 A1 | 10/2014 | Kerkhoffs et al. | |
| 2014/0316426 A1 | 10/2014 | Gollner et al. | |
| 2015/0054336 A1 | 2/2015 | Xinfang | |
| 2015/0167659 A1 | 6/2015 | Sauer | |
| 2015/0273124 A1 | 10/2015 | Callaway et al. | |
| 2015/0330383 A1 | 11/2015 | Letailleur et al. | |
| 2015/0374906 A1 | 12/2015 | Forsell | |
| 2016/0038664 A1 | 2/2016 | Callaway et al. | |
| 2016/0051738 A1 | 2/2016 | Callaway et al. | |
| 2016/0235899 A1 | 8/2016 | Yu et al. | |
| 2016/0243294 A1 | 8/2016 | Peters et al. | |
| 2017/0000934 A1 | 1/2017 | Miyakoshi | |
| 2017/0012491 A1 | 1/2017 | Schob et al. | |
| 2017/0266358 A1 | 9/2017 | Aber | |
| 2017/0290966 A1 | 10/2017 | Botterbusch et al. | |
| 2017/0290967 A1* | 10/2017 | Botterbusch | A61M 60/148 |
| 2017/0296723 A1 | 10/2017 | Garrigue | |
| 2018/0038364 A1 | 2/2018 | Dumas et al. | |
| 2018/0050143 A1* | 2/2018 | Nguyen | A61M 60/863 |
| 2018/0256798 A1 | 9/2018 | Botterbusch et al. | |
| 2018/0369469 A1 | 12/2018 | Le Duc De Lillers et al. | |
| 2019/0125949 A1 | 5/2019 | Botterbusch et al. | |
| 2019/0268332 A1 | 8/2019 | Wang | |
| 2019/0381227 A1 | 12/2019 | Botterbusch et al. | |
| 2020/0368417 A1 | 11/2020 | Polverelli et al. | |
| 2021/0085845 A1 | 3/2021 | West | |
| 2021/0170160 A1 | 6/2021 | Le Duc De Lillers et al. | |
| 2021/0172429 A1 | 6/2021 | Drevet et al. | |
| 2021/0275797 A1 | 9/2021 | Snyder et al. | |
| 2021/0330960 A1 | 10/2021 | Hall et al. | |
| 2021/0379353 A1 | 12/2021 | Botterbusch et al. | |
| 2022/0016412 A1 | 1/2022 | Bourquin et al. | |

FOREIGN PATENT DOCUMENTS

| | | | | |
|---|---|---|---|---|
| AU | 2013203301 B2 | 10/2015 | | |
| CA | 2712945 A1 | 7/2009 | | |
| CN | 1257006 A | 6/2000 | | |
| CN | 1355715 A | 6/2002 | | |
| CN | 1714759 A | 1/2006 | | |
| CN | 101472627 A | 7/2009 | | |
| CN | 101878049 A | 11/2010 | | |
| CN | 102112744 A | 6/2011 | | |
| CN | 102284092 A | 12/2011 | | |
| CN | 106421939 A | 2/2017 | | |
| CN | 106489026 A | 3/2017 | | |
| CN | 107635602 A | 1/2018 | | |
| CN | 108514661 A | * | 9/2018 | A61M 1/101 |
| CN | 114367029 A | 4/2022 | | |
| CN | 114470512 A | 5/2022 | | |
| EP | 0412856 A1 | 2/1991 | | |
| EP | 0415949 A1 | 3/1991 | | |
| EP | 0412856 B1 | 1/1994 | | |
| EP | 0445782 B1 | 8/1994 | | |
| EP | 0925081 B1 | 12/2003 | | |
| EP | 0961621 B1 | 7/2004 | | |
| EP | 1551500 A2 | 7/2005 | | |
| EP | 1233797 B1 | 7/2006 | | |
| EP | 1337288 B1 | 3/2008 | | |
| EP | 1981585 A2 | 10/2008 | | |
| EP | 1644639 B1 | 2/2009 | | |
| EP | 2152339 A1 | 2/2010 | | |
| EP | 2249746 A1 | 11/2010 | | |
| EP | 2310067 A1 | 4/2011 | | |
| EP | 2600918 A1 | 6/2013 | | |
| EP | 2517739 B1 | 12/2013 | | |
| EP | 2704761 A1 | 3/2014 | | |
| EP | 2310067 B1 | 4/2014 | | |
| EP | 2753389 A1 | 7/2014 | | |
| EP | 2152339 B1 | 5/2015 | | |
| EP | 2891502 A1 | 7/2015 | | |
| EP | 2704761 B1 | 9/2015 | | |
| EP | 2736552 B1 | 9/2015 | | |
| EP | 2891502 B1 | 7/2016 | | |
| EP | 2164542 B1 | 8/2016 | | |
| EP | 2856190 B1 | 9/2016 | | |
| EP | 3141269 A1 | * | 3/2017 | A61M 1/1008 |
| EP | 3145558 A2 | 3/2017 | | |
| ES | 2587072 A1 | 10/2016 | | |
| FR | 355700 A | 11/1905 | | |
| FR | 2650862 B1 | 11/1991 | | |
| FR | 2744769 A1 | 8/1997 | | |
| FR | 2744769 B1 | 2/1999 | | |
| FR | 2861910 B1 | 1/2006 | | |
| FR | 2905147 A1 | 2/2008 | | |
| FR | 3032917 A1 | 8/2016 | | |
| GB | 662047 A | 11/1951 | | |
| JP | 2011509801 A | 3/2011 | | |
| KR | 20130068373 A | 6/2013 | | |
| WO | WO-8910763 A1 | 11/1989 | | |
| WO | WO-9008260 A1 | 7/1990 | | |
| WO | WO-9729282 A1 | 8/1997 | | |
| WO | WO-9959652 A1 | 11/1999 | | |
| WO | WO-0037126 A1 | 6/2000 | | |
| WO | WO-0074747 A1 | 12/2000 | | |
| WO | WO-2007053881 A1 | 5/2007 | | |
| WO | WO-2011056823 A2 | 5/2011 | | |
| WO | WO-2016179262 A1 | 11/2016 | | |
| WO | WO-2017087717 A1 | 5/2017 | | |
| WO | WO-2017087785 A1 | 5/2017 | | |
| WO | WO-2019019206 A1 | 1/2019 | | |
| WO | WO-2019092175 A1 | 5/2019 | | |
| WO | WO-2019154804 A1 | 8/2019 | | |
| WO | WO-2020115607 A2 | 6/2020 | | |
| WO | WO-2020155607 A1 | 8/2020 | | |

OTHER PUBLICATIONS

U.S. Appl. No. 15/484,108 / U.S. Pat. No. 10,166,319, filed Apr. 10, 2017 / Jan. 1, 2019.
U.S. Appl. No. 15/940,856 / U.S. Pat. No. 10,933,181, filed Mar. 29, 2018 / Mar. 2, 2021.
U.S. Appl. No. 15/953,269 / U.S. Pat. No. 10,188,779, filed Apr. 13, 2018 / Jan. 29, 2019.
U.S. Appl. No. 15/976,831 / U.S. Pat. No. 10,398,821, filed May 10, 2018 / Sep. 3, 2019.
U.S. Appl. No. 16/234,519, filed Dec. 27, 2018.
U.S. Appl. No. 16/557,711, filed Aug. 30, 2019.
U.S. Appl. No. 16/762,909, filed May 8, 2019.
U.S. Appl. No. 16/766,267, filed May 21, 2020.
U.S. Appl. No. 16/819,021 / U.S. Pat. No. 10,799,625, filed Mar. 13, 2020 / Oct. 31. 2020.
U.S. Appl. No. 17/179,961, filed Feb. 19, 2021.
U.S. Appl. No. 17/193,867, filed Mar. 5, 2021.
International Search Report & Written Opinion dated Apr. 2, 2024 in Int'l PCT Patent Appl. Serial No. PCT/IB2023/061509 (1310).

(56) References Cited

OTHER PUBLICATIONS

Ando, et al., Electrocardiogram-Synchronized Rotational Speed Change Mode in Rotary Pumps Could Improve Pulsatility, Artificial Organs, 35(10):941-947 (2011).
Ando, et al., Left ventricular decompression through a patent foramen ovale in a patient with hypertrophic cardiomyopathy: A case report, Cardiovascular Ultrasound, 2: 1-7 (2004).
Bozkurt, et al., Improving Arterial Pulsatility by Feedback Control of a Continuous Flow Left Ventricular Assist Device via in silico Modeling, International Journal of Artificial Organs, 37(10):773-785 (2014).
Castellanos, et al., Generations of Left Ventricular Assist Devices: The HeartMate Family, Dept. of Bioengineering. Florida Gulf Coast University, BME 3100C, pp. 1-6. (No date available).
Crow, et al., Gastrointestinal Bleeding Rates in Recipients of Nonpulsatile and Pulsatile Left Ventricular Assist Devices, The Journal of Thoracic and Cardiovascular Surgery, 137(1):208-215 (2009).
Fatullayev, et al., Continuous-Flow Left Ventricular Assist Device Thrombosis: A Danger Foreseen is a Danger Avoided, Medical Science Monitor Basic Research, 21:141-144 (2015).
Feier, et al., A Novel, Valveless Ventricular Assist Device: The Fish Tail Pump. First Experimental in Vivo Studies, Artificial Organs, (26)12:1026-1031 (2002).
Fliess, et al., Flatness and Defect of Nonlinear Systems: Introductory Theory and Examples, International Journal of Control, 61(6):1327-1361 (1995).
Fraser et al., A Quantitative Comparison of Mechanical Blood Damage Parameters in Rotary Ventricular Assist Devices: Shear Stress, Exposure Time and Hemolysis Index, Journal of Biomechanical Engineering, 134(8):018002-1 to 018002-11 (2012).
Harris, et al., Ventricular Assist Devices, Continuing Education in Anesthesia, Critical Care & Pain, 12(3):145-151 (2012).
International Search Report & Written Opinion dated Mar. 4, 2019 in Int'l PCT Patent Appl. No. PCT/IB2018/059199 (0510).
International Search Report & Written Opinion dated May 14, 2021 in Int'l PCT Patent Appl. Serial No. PCT/IB2021/051879 (0910).
International Search Report & Written Opinion dated Jun. 28, 2017 in Int'l PCT Patent Appl. Serial No. PCT/IB2017/052068 (0210).
International Search Report & Written Opinion dated Jul. 15, 2020 in Int'l PCT Patent Appl. Serial No. PCT/IB2019/060144 (0610).
International Search Report & Written Opinion dated Aug. 22, 2017 in Int'l PCT Patent Appl. Serial No. PCT/IB2017/052069 (0310).
International Search Report & Written Opinion dated Apr. 16, 2019 in Int'l PCT Patent Appl. Serial No. PCT/EP2018/080749 (English Translation of ISR only) (0810).
International Search Report & Written Opinion dated Jun. 25, 2020 in International PCT Patent Appl. Serial No. PCT/1B2020/052337 (0710).
International Search Report & Written Opinion dated Aug. 3, 2018 in Int'l PCT Patent Appl. Serial No. PCT/IB2018/052215 (0410).
Ising, M., RPM and Flow Modulation for a Continuous Flow Left Ventricular Assist Device to Increase Vascular Pulsatility: A Computer Simulation, Mock Circulation, and In-Vivo Animal Study, University of Louisville, Think IR: The University of Louisville's Institutional Repository, Electronic Theses and Dissertations (Jul. 2011).
Islam et al., Left Ventricular Assist Devices and Gastrointestinal Bleeding: A Narrative Review of Case Reports and Case Series, Clinical Cardiology, 36(4):190-200 (2013).
Jorde, et al., Identification and Management of Pump Thrombus in the HeartWare Left Ventricular Assist Device System, JACC: Heart Failure, 3(11):849-856 (2015).
Latham, et al., Parameter Estimation and a Series of Nonlinear Observers for the System Dynamics of a Linear Vapor Compressor, IEEE Transactions on Industrial Electronics, 63(11):6736-6744 (2016).
Leverett, et al., Red Blood Cell Damage by Shear Stress, Biophysical Journal, 12(3):257-273 (1972).
Malehsa, et al., Acquired von Willebrand Syndrome After Exchange of the HeartMate XVE to the HeartMate II Ventricular Assist Device, European Journal of Cardio-Thoracic Surgery, 35(6):1091-1093 (2009).
Mancini, et al., Left Ventricular Assist Devices, A Rapidly Evolving Alternative to Transplant, Journal of the American College of Cardiology, 653:2542-2555 (2015).
Mboup, et al., Numerical Differentiation With Annihilators in Noisy Environment, Numerical Algorithms, 50(4):439-467 (2009).
Menhour, et al., An Efficient Model-Free Setting for Longitudinal and Lateral Vehicle Control: Validation Through the Interconnected Pro-SiVIC/RTMaps Prototyping Platform, IEEE Transactions on Intelligent Transportation Systems, 19(2):461-475 (2018).
Mercorelli, P., A Motion-Sensorless Control for Intake Valves in Combustion Engines, IEEE Transactions on Industrial Electronics, 64(4):3402-3412 (2017).
Mercorelli, P., An Adaptive and Optimized Switching Observer for Sensorless Control of an Electromagnetic Valve Actuator in Camless Internal Combustion Engines, Asian Journal of Control, 16(4):959-973 (2014).
Mohite, et al., Does CircuLite Synergy Assist Device as Partial Ventricular Support have a Place in Modern Management of Advanced Heart Failure?, Expert Rev. Med. Devices, published online Dec. 2, 2014 (pp. 1-12).
Najjar, et al., An Analysis of Pump Thrombus Events in Patients in HeartWare Advance Bridge to Transplant and Continued Access Protocol Trial, The Journal of Heart and Lung Transplantation, 33(1):23-34 (2014).
Pagani, Francis D., MD, PhD, Department of Cardiac Surgery, University of Michigan, "Technology 101: Review of Current Technologies, Types of Flow, Pump Parameters," American Association for Thoracic Surgery, Annual Meeting (2014), Cardiothoracic Transplant and Mechanical Circulatory Support of Heart and Lung Failure.
Perschall, et al., The Progressive Wave Pump: Numerical Multiphysics Investigation of a Novel Pump Concept With Potential to Ventricular Assist Device Application, Artificial Organs, 35(9):E179-E190 (2012).
Rahman, et al., Position Estimation in Solenoid Actuators, IEEE Transactions on Industry Applications, 32(3):552-559 (1996).
Rigatos, G., Differential Flatness Theory ad Flatness-Based Control, in Nonlinear Control and Filtering Using Differential Flatness Approaches, 25(2):47-101 (2015).
Wang, et al., Rotary Blood Pump Control Strategy for Preventing Left Ventricular Suction, ASAIO Journal, 61(1):21-30(2015).
Wang., Quadrotor Analysis and Model Free Control with Comparisons, Universite Paris Sud—Paris XI, (2013).
Weidemann, Daniel., Thesis entitled, Permanent Magnet Reluctance Actuators for Vibration Testing, Completed at the Institute of Applied Mechanics, Technische Universitat Munchen, Apr. 2013.
Yuan, et al., The Spectrum of Complications Following Left Ventricular Assist Device Placement, Journal of Cardiac Surgery, 27:630-638 (2012).
Zhang, et al., Study on Self-Sensor of Linear Moving Magnet Compressor's Piston Stroke, IEEE Sensors Journal, 9(2):154-158 (2009).
International Search Report & Written Opinion dated Jun. 30, 2025 in Int'l PCT Patent Appl. Serial No. PCT/IB2025/053546 (141001).
Extended European Search Report dated Aug. 25, 2021 in EP Patent Application Serial No. 21168340.4 (0231).
International Search Report & Written Opinion dated Oct. 9, 2023 in Int'l PCT Patent Appl. Serial No. PCT/IB2023/054203 (1110).

* cited by examiner

APPARATUS AND METHODS FOR COUPLING A BLOOD PUMP TO THE HEART

CROSS-REFERENCE TO RELATED APPLICATIONS

This application is a national phase application under 35 U.S.C. § 371 of PCT/IB2019/060144, filed Nov. 26, 2019, which claims priority to U.S. Provisional Patent Application No. 62/775,888, filed Dec. 5, 2018, the entire contents of each of which are incorporated herein by reference.

FIELD OF THE INVENTION

This application generally relates to apparatus and methods for coupling a blood pump to the heart.

BACKGROUND OF THE INVENTION

The human heart is comprised of four major chambers with two ventricles and two atria. Generally, the right-side heart receives oxygen-poor blood from the body into the right atrium and pumps it via the right ventricle to the lungs. The left-side heart receives oxygen-rich blood from the lungs into the left atrium and pumps it via the left ventricle to the aorta for distribution throughout the body. Due to any of a number of illnesses, including coronary artery disease, high blood pressure (hypertension), valvular regurgitation and calcification, damage to the heart muscle as a result of infarction or ischemia, myocarditis, congenital heart defects, abnormal heart rhythms or various infectious diseases, the left ventricle may be rendered less effective and thus unable to adequately pump oxygenated blood throughout the body.

The Centers for Disease Control and Prevention (CDC) estimates that about 5.1 million people in the United States suffer from some form of heart failure. Heart failure is generally categorized into four different stages with the most severe being end stage heart failure. End stage heart failure may be diagnosed where a patient has heart failure symptoms at rest in spite of medical treatment. Patients at this stage may have systolic heart failure, characterized by decreased ejection fraction. In patients with systolic heart failure, the walls of the ventricle are weak and do not squeeze as forcefully as a healthy patient. Consequently, during systole a reduced volume of oxygenated blood is ejected into circulation, a situation that continues in a downward spiral until death. Patients may alternatively have diastolic heart failure wherein the heart muscle becomes stiff or thickened making it difficult for the affected chamber to fill with blood. A patient diagnosed with end stage heart failure has a one-year mortality rate of approximately 50%.

For patients that have reached end stage heart failure, treatment options are limited. In addition to continued use of drug therapy commonly prescribed during earlier stages of heart failure, cardiac transplantation and implantation of a mechanical assist device are typically recommended. While a cardiac transplant may significantly prolong the patient's life beyond the one year mortality rate, patients frequently expire while on a waitlist for months and sometimes years awaiting a suitable donor heart. Presently, the only alternative to a cardiac transplant is a mechanical implant. While in recent years mechanical implants have improved in design, typically such implants will prolong a patient's life by a few years at most, and include a number of co-morbidities.

One type of mechanical implant often used for patients with end stage heart failure is a left ventricular assist device (LVAD). The LVAD is a surgically implanted pump that draws oxygenated blood from the left ventricle and pumps it directly to the aorta, thereby off-loading (reducing) the pumping work of the left ventricle. LVADs typically are used either as "bridge-to-transplant therapy" or "destination therapy." When used for bridge-to-transplant therapy, the LVAD is used to prolong the life of a patient who is waiting for a heart transplant. When a patient is not suitable for a heart transplant, the LVAD may be used as a destination therapy to prolong the life, or improve the quality of life, of the patient, but generally such prolongation is for only a couple years.

Notwithstanding the type of LVAD device employed, an LVAD generally includes an inflow cannula, a pump, and an outflow cannula, and is coupled to an extracorporeal battery and control unit. The inflow cannula typically directly connects to the left ventricle, e.g., at the apex, and delivers blood from the left ventricle to the pump. The outflow cannula typically extends outside of the heart and includes an extra-cardiac return line that is routed through the upper chest and connects to the aorta distal to the aortic valve. As such the outflow cannula delivers blood from the pump to the aorta via the return line, which typically consists of a tubular structure, such as a Dacron graft, that is coupled to the aorta via an anastomosis. A sternotomy or thoracotomy is required to implant the pump within the patient. In addition, a separate aortic anastomosis procedure is also required to connect the pump to the aorta.

What is a needed is a more efficient apparatus and method for removeably coupling the inflow cannula of the blood pump to the heart, e.g., at the apex of the heart, such that the inflow cannula is in fluidic communication with the left ventricle of the heart.

SUMMARY OF THE INVENTION

The present invention overcomes the drawbacks of previously-known devices by providing an apparatus for coupling a blood pump to a patient's heart. The apparatus includes a sewing ring designed to be sutured to the patient's heart, wherein the sewing ring has an opening sized and shaped to receive an inflow cannula of the blood pump. The apparatus further includes a locking element coupled to a housing of the blood pump and transitionable between a closed state and an open state. The locking element is structured to receive the sewing ring in the open state and engage the sewing ring in the closed state to prevent translational and rotational movement of the locking element relative to the sewing ring. In addition, the apparatus includes a biased structure designed to bias the locking element in the closed state.

For example, in accordance with one aspect of the present invention, the locking element may include a plurality of horizontal crenellations disposed along a circumferential opening of the locking element, the plurality of horizontal crenellations of the locking device separated by a plurality of gaps, the plurality of gaps sized and shaped to receive a plurality of horizontal crenellations disposed adjacent the opening of the sewing ring when the locking element is in the open state. Accordingly, in the closed state, the plurality of horizontal crenellations of the locking element are aligned with the horizontal crenellations of the sewing ring to prevent translational movement of the locking element relative to the sewing ring. In addition, the housing of the blood pump may include a plurality of vertical crenellations, the plurality of vertical crenellations of the housing of the blood pump sized and shaped to receive corresponding indentations of the sewing ring to prevent rotational movement of the locking element relative to the sewing ring.

In this embodiment, the biased structure may include a first end and a second end, such that the biased structure is disposed circumferentially about a longitudinal axis of the blood pump between the first and second ends. The first end of the biased structure may be coupled to the housing of the blood pump, and the second end of the biased structure may be coupled to the locking element via a locking pin. The locking pin may be moveable within a groove on the housing of the blood pump to permit movement of the second end of the biased structure. Further, the locking element is designed to rotate about a longitudinal axis of the housing of the blood pump to transition from the closed state to the open state. Accordingly, rotation of the locking element causes the second end of the biased structure to move from a first position in the closed state to a second position toward the first end in the open state, thereby compressing the biased structure in the open state.

Moreover, the locking element may include a plurality of brackets designed to engage with the housing of the blood pump. The plurality of brackets each have a groove sized and sized to accept one or more guide rails disposed on a surface of the housing of the blood pump such that the plurality of brackets moves along the one or more guide rails as the locking element transitions between the closed state and the open state. In addition, the housing of the blood pump may include a stop designed to limit rotation of the locking element relative to the housing of the blood pump. Accordingly, a notch of the locking element may engage the stop in the open state.

In accordance with another aspect of the present invention, the locking element includes one or more hook portions designed to engage with the sewing ring in the closed state. For example, the locking element may include two hook portions, the two hook portions positioned opposite one another along the housing of the blood pump. The one or more hook portions may include a sloped surface such that contact between the sloped surface of the one or more hook portions and an inner surface of the sewing ring causes the one or more hook portions to move radially inward toward the inflow cannula of the blood pump. Accordingly, the sewing ring may include one or more slots sized and shaped to receive the one or more hook portions of the locking element in the closed state.

The locking element may move from a first position in the closed state to a second position radially inward toward the inflow cannula of the blood pump in the open state. In this embodiment, the biased structure is disposed circumferentially about a longitudinal axis of the blood pump, such that the biased structure is compressed when the locking element is in the second position. In addition, the biased structure includes first and second ends sized and shaped to slidably move radially along first and second grooves of the housing of the pump body, wherein the first and second tabs are positioned opposite one another and 45 degrees from the locking element. Moreover, the apparatus may include a hood having an opening sized and shaped to receive the locking element therethrough.

In accordance with yet another aspect of the present invention, a method for coupling a blood pump to a patient's heart is provided. The method includes suturing the sewing ring to the patient's heart, transitioning the locking element coupled to the housing of the blood pump from the closed state to the open state, inserting the inflow cannula of the blood pump through the opening of the sewing ring and engaging the sewing ring with the locking element in the open state, and transitioning the locking element from the open state to the closed state to prevent translational and rotational movement of the locking element relative to the sewing ring.

For example, in the embodiment where the locking element includes a plurality of horizontal crenellations disposed along the circumferential opening of the locking element, engaging the sewing ring with the locking element in the open state includes aligning the plurality of gaps of the locking element with the plurality of horizontal crenellations of the sewing ring. Accordingly, transitioning the locking element from the open state to the closed state may include aligning the plurality of horizontal crenellations of the locking device the plurality of horizontal crenellations of the sewing ring to prevent translational movement of the locking element relative to the sewing ring. In addition, in the embodiment where the locking element includes one or more hook portions, transitioning the locking element from the open state to the closed state comprises moving the locking element from the first position in the closed state to the second position radially inward toward the inflow cannula of the blood pump in the open state.

DETAILED DESCRIPTION OF THE INVENTION

Embodiments of the present invention are directed to apparatus and methods for removeably coupling the inflow cannula of the blood pump to the heart.

Figure 1:
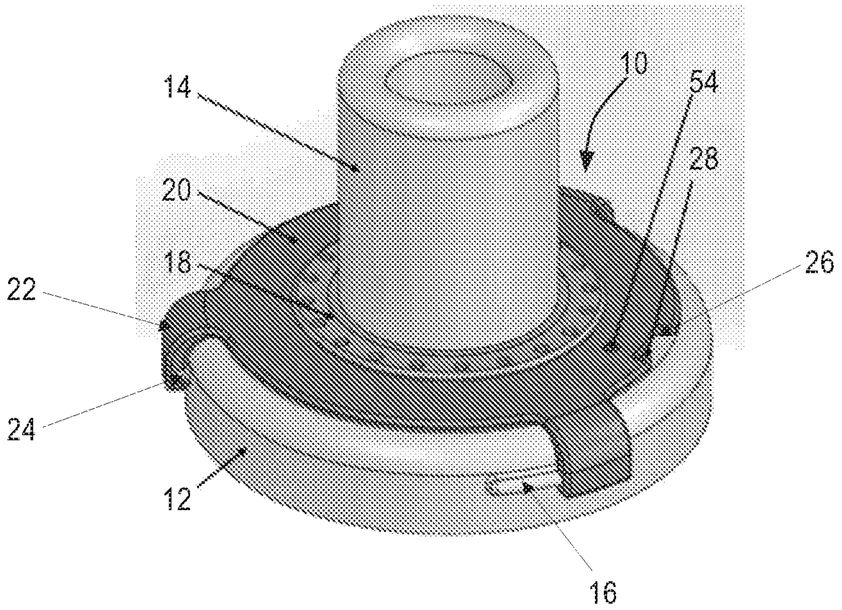
FIG. 1 illustrates an exemplary locking mechanism for coupling a heart pump to the heart constructed in accordance with the principles of the present invention.

Referring now to FIG. 1, an exemplary locking mechanism for coupling a heart pump to the heart constructed in accordance with the principles of the present invention is provided. Locking mechanism 10 is includes sewing ring 18 designed to be sutured to a patient's heart, and locking element 20 coupled to a housing of blood pump 12, wherein locking element 20 is designed to be removeably coupled to sewing ring 18, and thus, the patient's heart. As described in further detail below, locking element 20 may be rotated from a closed state to an open state to receive sewing ring 18, and back to the closed state to lock sewing ring 18 with locking element 20 to prevent translational and rotational movement of locking element 20 relative to sewing ring 18.

Blood pump 12 may be any heart pump designed to be affixed to a patient's heart, e.g., an LVAD designed to shunt blood from the left ventricle to the aorta of the heart such as the heart pumps disclosed in U.S. Pat. No. 9,968,720 to Botterbusch, U.S. Pat. No. 10,166,319 to Botterbusch, and U.S. Pat. No. 10,188,779 to Polverelli, assigned to the assignee of the instant application, the entire contents of each of which are incorporated herein by reference. For example, blood pump 12 includes inflow cannula 14 for receiving blood from a source of blood, e.g., the left ventricle of the heart. Inflow cannula 14 has a cylindrical shape and is positioned at the upper portion of blood pump 12.

Sewing ring 18 includes a fabric portion (not shown) that may be sutured to the heart using methods already known in the art of cardiology, and a metal portion that is designed to be removeably coupled to locking element 20. Locking element 20 includes opening 11 sized and shaped to receive inflow cannula 14 of blood pump 12. In addition, as shown in FIG. 1, locking element 20 includes three brackets 22 extending from the periphery of locking element 20, and curving downward to engage with the external side surface of the housing of blood pump 12. For example, each of brackets 22 includes grooved surface 24 sized and shaped for receiving guild rails 16 positioned about external side surface of the housing of blood pump 12, such that locking element 20 may rotate about the longitudinal axis of blood pump 12 along guide rails 16. As will be understood by a person ordinarily skilled in the art, locking element 20 may include fewer or more than three brackets, and thus, house pump 12 may include fewer or more than three guide rails, e.g., one, two, four, or more brackets and guide rails. Alternatively, the housing of blood pump 12 may have a number of guide rails less than the number of brackets, e.g., one guide rail extending partially or completely around the circumference of the housing of blood pump 12.

As illustrated in FIG. 1, locking element 26 includes notch 26 sized and shaped to engage with stop 28 coupled to the housing of blood pump 12 during rotation of locking element 20. For example, in the open state, one end of notch 26 is adjacent stop 28, and as locking element 20 is rotated about the longitudinal axis of blood pump 12, notch 26 moves along stop 28 until stop 26 engages with the opposite end of notch 26. Thus, stop 26 limits rotation of locking element 20 so that locking element 20 may easily be rotated and cease rotation in the open state.

Figure 2A:
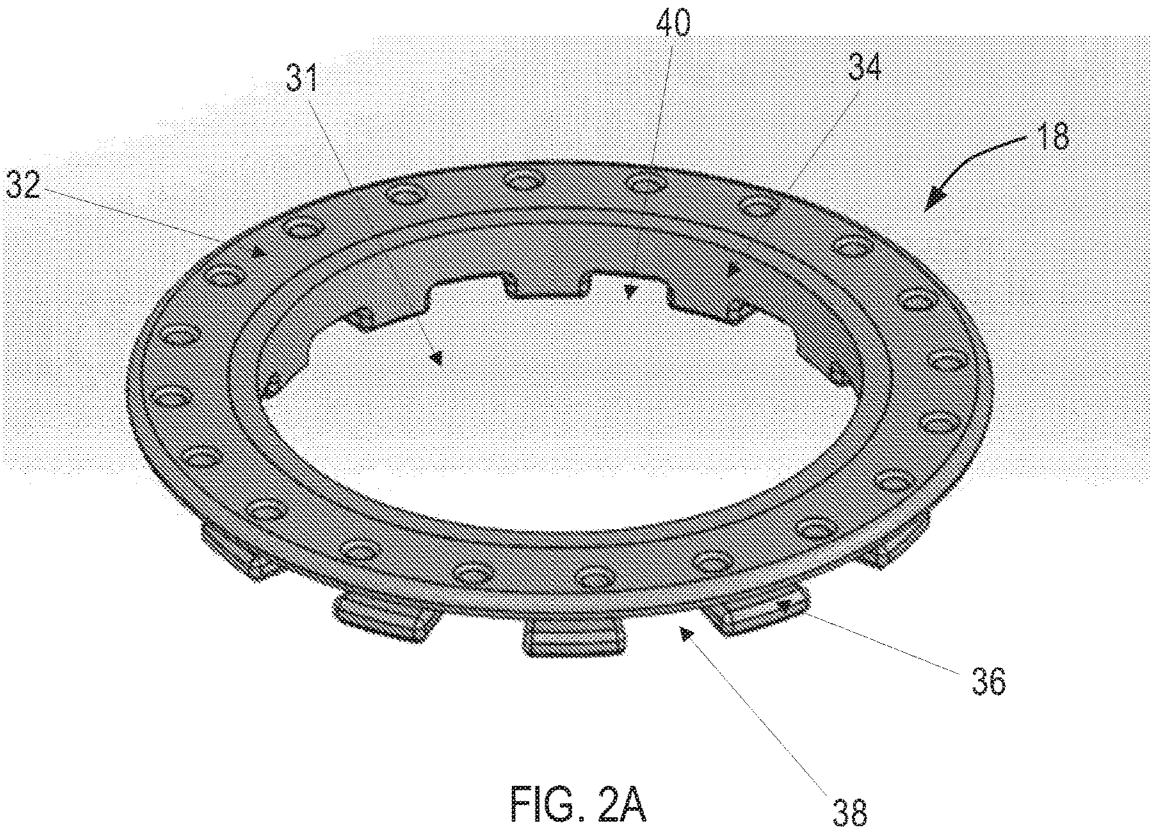
FIGS. 2A and 2B illustrate the exemplary sewing ring of FIG. 1.
Figure 2B:
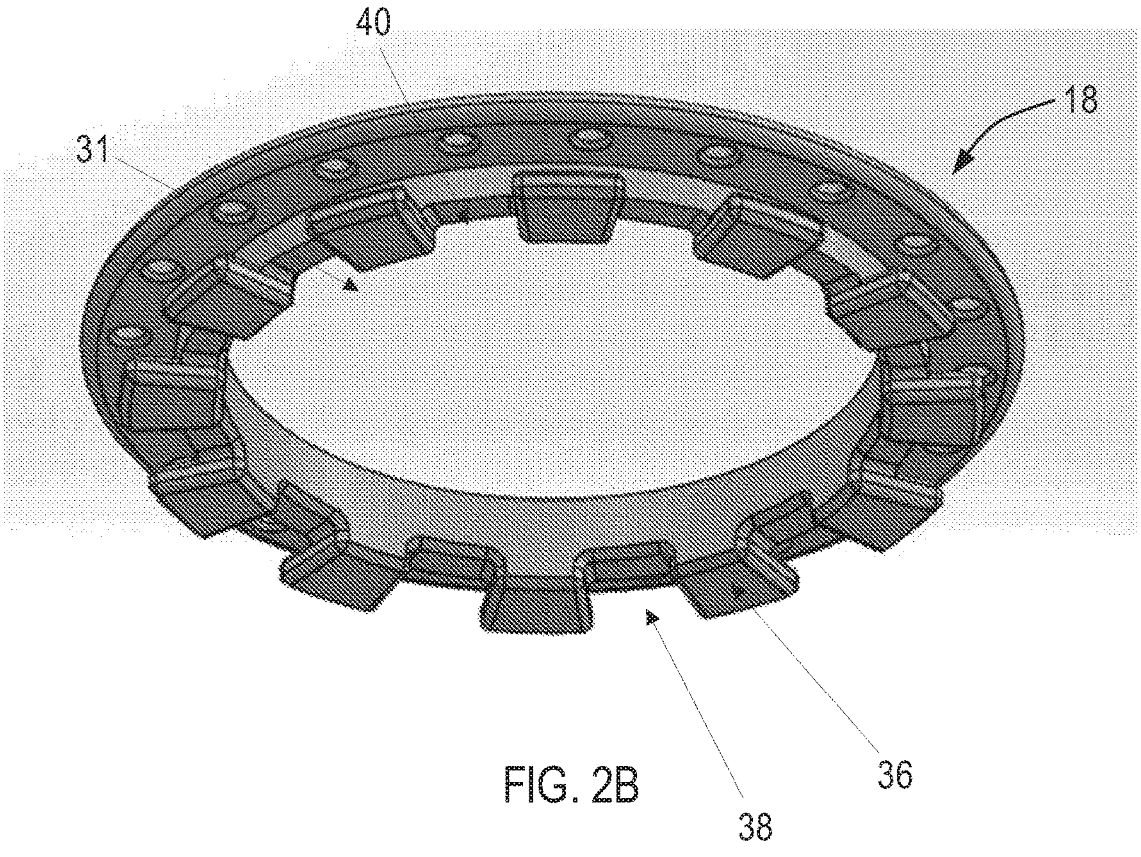

Referring now to FIGS. 2A and 2B, sewing ring 18 is described. Sewing ring 18 has opening 31 sized and shaped to receive inflow cannula 14 of blood pump 12. Sewing ring 18 includes planar portion 32 extending circumferentially forming opening 31, and vertical portion 34 extending downward from the inner edge of planar portion 32 adjacent opening 31 of sewing ring 18. The lower edge of vertical portion 34 includes a pattern of horizontal crenellations 36 separated by gaps 38, such that the pattern of horizontal crenellations 36 extend in a radial direction outward toward the outer periphery of sewing ring 18. In addition, the lower edge of vertical portion 34 includes a pattern of vertical indentations 40 separated by the portions of horizontal crenellations 36 coupled to the lower edge of vertical portion 34.

Figure 3:
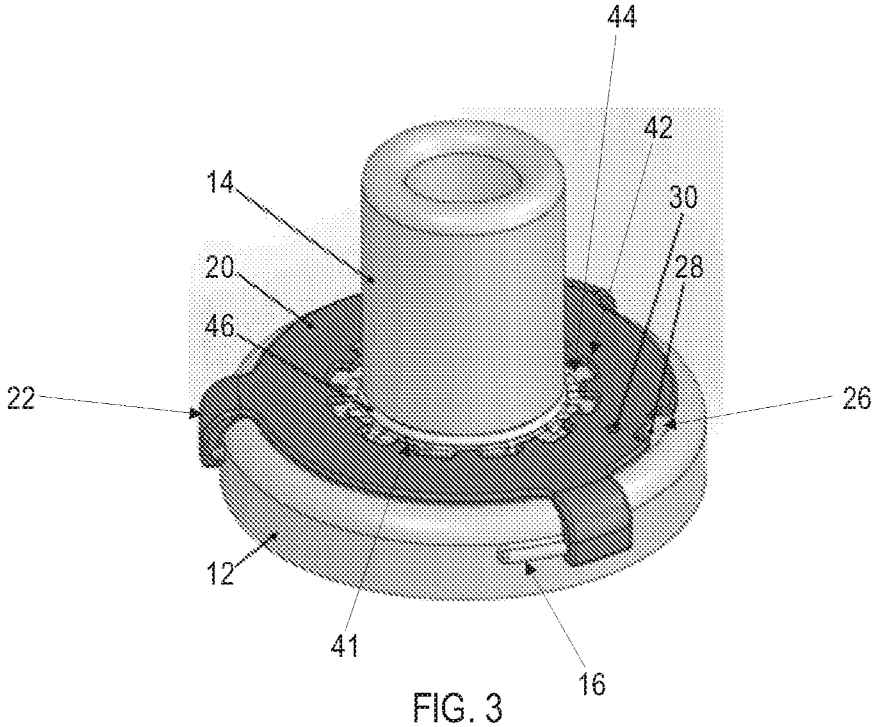
FIG. 3 illustrates the locking mechanism of FIG. 1 without the sewing ring.

As illustrated in FIG. 3, locking element 20 includes a pattern of horizontal crenellations 41 extending toward inner cannula 14 of blood pump 12, separated by gaps 42 along the inner edge of locking element 20 adjacent opening 11. Gaps 42 of locking element 20 are sized and shaped to receive horizontal crenellations 36 of sewing ring 18 therethrough. For example, locking element 20 may be rotated about the longitudinal axis of blood pump 12, e.g., in a clockwise direction, until notice 26 engages with stop 28 such that locking element 20 is in an open state. After horizontal crenellations 36 of sewing ring 18 are received through gaps 42 of locking element 20, locking element 20 may be rotated about the longitudinal axis of blood pump 12 in the opposite direction, e.g., in a counter-clockwise direction such that horizontal crenellations 41 are aligned with horizontal crenellations 36 of sewing ring 18, thus preventing translational movement of sewing ring 18 relative to locking element 20, e.g., along the longitudinal axis of blood pump 12. As described in further detail below, locking element 20 may be bias toward the closed state such that after locking element 20 is moved to the open state to receive sewing ring 18, locking element 20 may automatically return to the closed state upon release of locking element 20.

The housing of blood pump 12 further may include a pattern of vertical crenellations 44 disposed circumferentially about the upper surface of the housing of blood pump 12 adjacent to inflow cannula 14. Vertical crenellations 44 are sized and shaped to be received within vertical indentations 40 of sewing ring 18 such that when sewing ring 18 is received within locking element 20, rotational movement of sewing 18 relative to locking element is prevented. In addition, the housing of blood pump 12 may include ring 46 made of, e.g., rubber, disposed circumferentially about the external surface of inflow cannula 14. Accordingly, inflow cannula 14 may include a groove disposed circumferentially about the external surface of inflow cannula 14, the groove sized and shaped to receive ring 46 to form an impermeable seal against vertical portion 34 of sewing ring 18.

Figure 4:
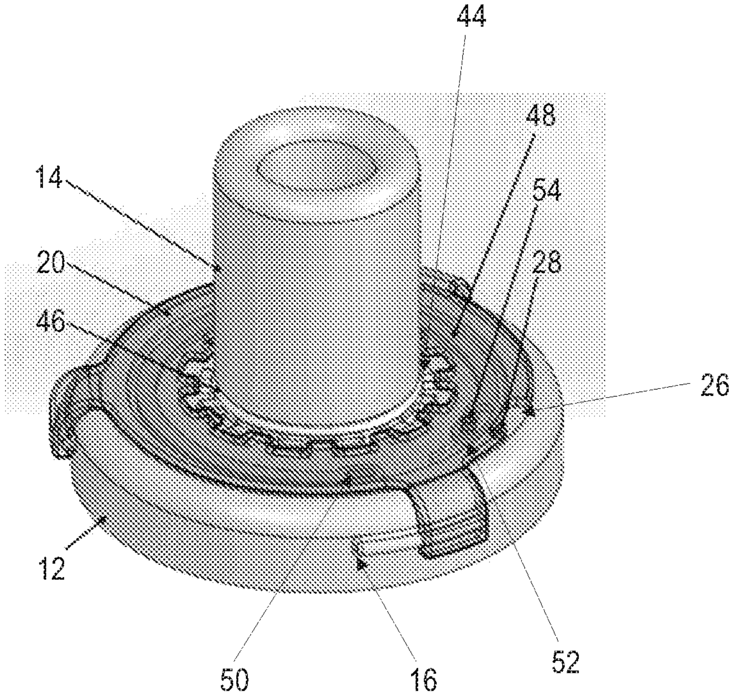
FIG. 4 illustrates the internal components of the locking mechanism of FIG. 3.

As illustrated in FIG. 4, locking mechanism 10 includes spring element 48. Spring element 48 includes first end 50 coupled to the upper surface of the housing of blood pump 12, and second end 52 is coupled to locking element 20 via locking pin 54. Second end 52 may include an opening for receiving locking pin 54 coupled to the locking element 20. In addition, the upper surface of the housing of blood pump 20 includes a groove sized and shaped to receive locking pin 54, such that locking pin 54 is moveable along the groove. Thus, an edge of the groove may limit further rotation of locking element 20 when locking pin 54 engages that edge of the groove. As locking element 20 is rotated from the closed state to the open state, locking pin 54 causes second end 52 of spring element 48 to move from a first position in the closed state to a second position closer to first end 50 in the open state. As first end 50 is fixed to the upper surface of the housing of blood pump 20, spring element 48 compresses as second end 52 moves from the first position to the second position. Upon release of locking element 20, spring element 48 returns to a relaxed state, and thus, second end 52 causes locking element 20 to return to the closed state via locking pin 54.

Figure 5A:
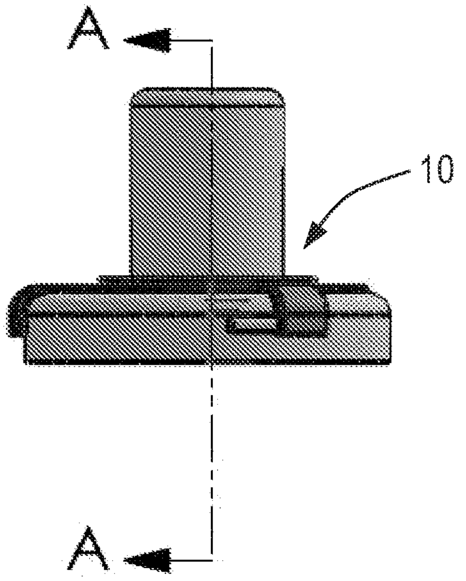
FIG. 5A illustrates a side view of the locking mechanism of FIG. 1, and FIGS. 5B and 5C illustrate a cross-sectional view of the locking mechanism of FIG. 5A.
Figure 5B:
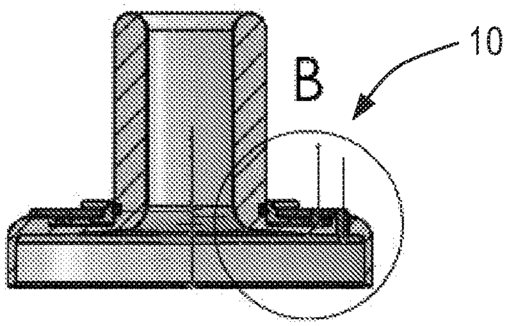
Figure 5C:
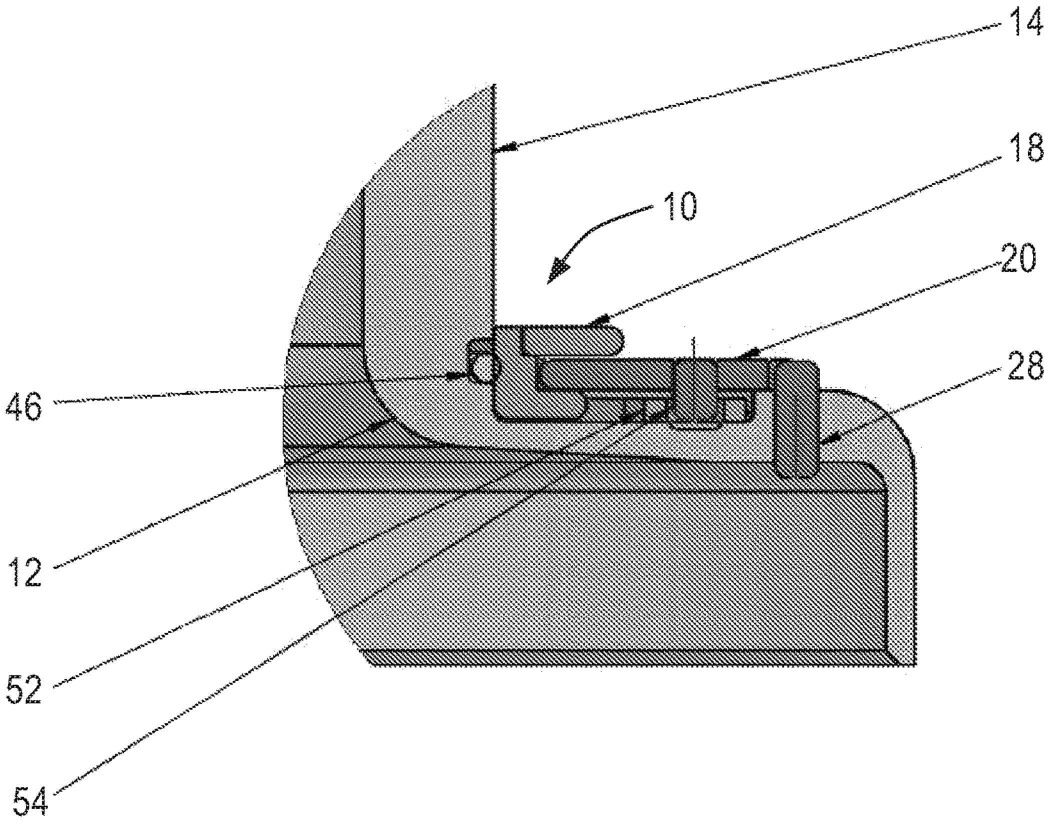

FIG. 5A illustrates a side view of locking mechanism 10 coupled to the housing of blood pump 12, and FIG. 5B illustrates a cross-sectional view of locking mechanism 10 coupled to the housing of blood pump 12 along line A-A of FIG. 5A. FIG. 5C illustrates an exploded view of circle B of FIG. 5B.

Figure 6:
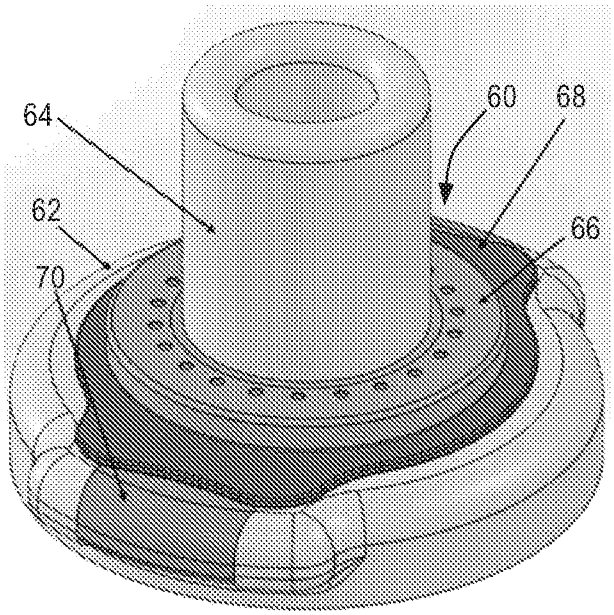
FIG. 6 illustrates another exemplary locking mechanism for coupling a heart pump to the heart constructed in accordance with the principles of the present invention.

Referring now to FIG. 6, another exemplary locking mechanism for coupling a heart pump to the heart constructed in accordance with the principles of the present invention is provided. Locking mechanism 60 includes sewing ring 66 designed to be sutured to a patient's heart, and locking element 70 coupled to a housing of blood pump 62, wherein locking element 70 is designed to be removeably coupled to sewing ring 66, and thus, the patient's heart. As described in further detail below, locking element 20 may be pushed inward from a closed state to an open state to receive sewing ring 66, and back to the closed state to lock sewing ring 66 with locking element 70 to prevent translational and rotational movement of locking element 70 relative to sewing ring 66.

Blood pump 62 may be any heart pump designed to be affixed to a patient's heart, e.g., an LVAD designed to shunt blood from the left ventricle to the aorta of the heart such as the heart pumps disclosed in U.S. Pat. No. 9,968,720 to Botterbusch, U.S. Pat. No. 10,166,319 to Botterbusch, and U.S. Pat. No. 10,188,779 to Polverelli, assigned to the assignee of the instant application, the entire contents of each of which are incorporated herein by reference. For example, blood pump 62 includes inflow cannula 64 for receiving blood from a source of blood, e.g., the left ventricle of the heart. Inflow cannula 64 has a cylindrical shape and is positioned at the upper portion of blood pump 62.

Sewing ring 66 includes a fabric portion (not shown) that may be sutured to the heart using methods already known in the art of cardiology, and a metal portion that is designed to be removeably coupled to locking element 70. In addition, locking mechanism 60 may include hood 68 positioned on the upper surface of the housing of blood pump 62, and over locking mechanism 70.

Figure 7A:
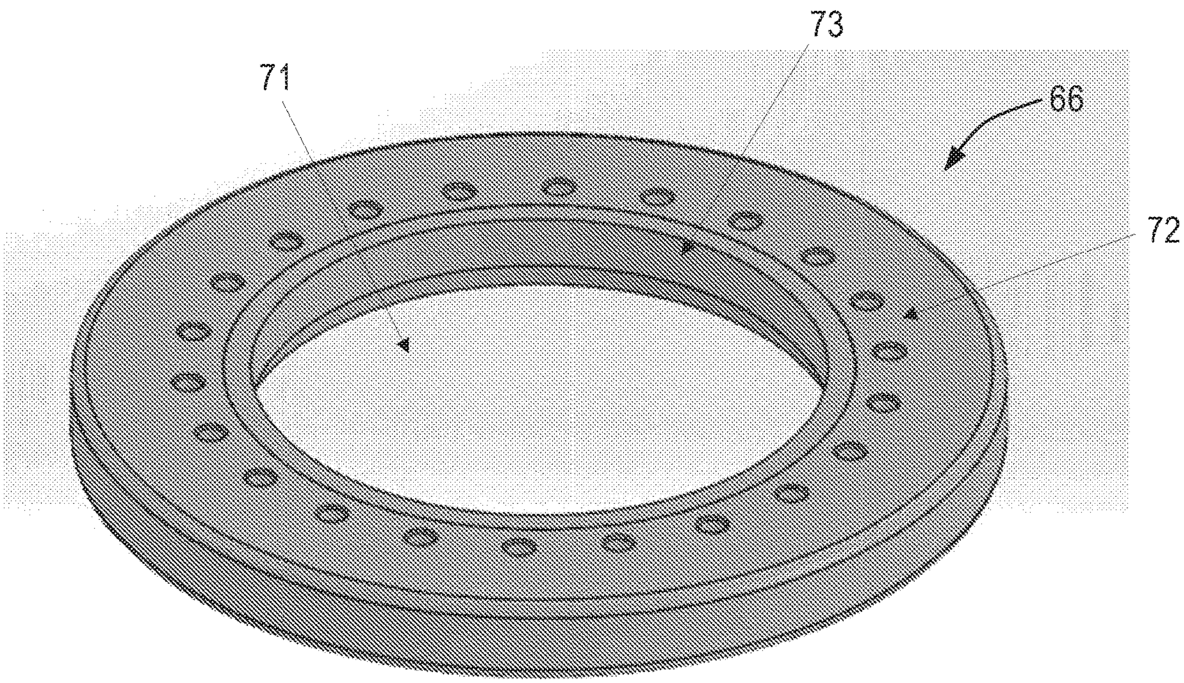
FIGS. 7A and 7B illustrate the exemplary sewing ring of FIG. 6.
Figure 7B:
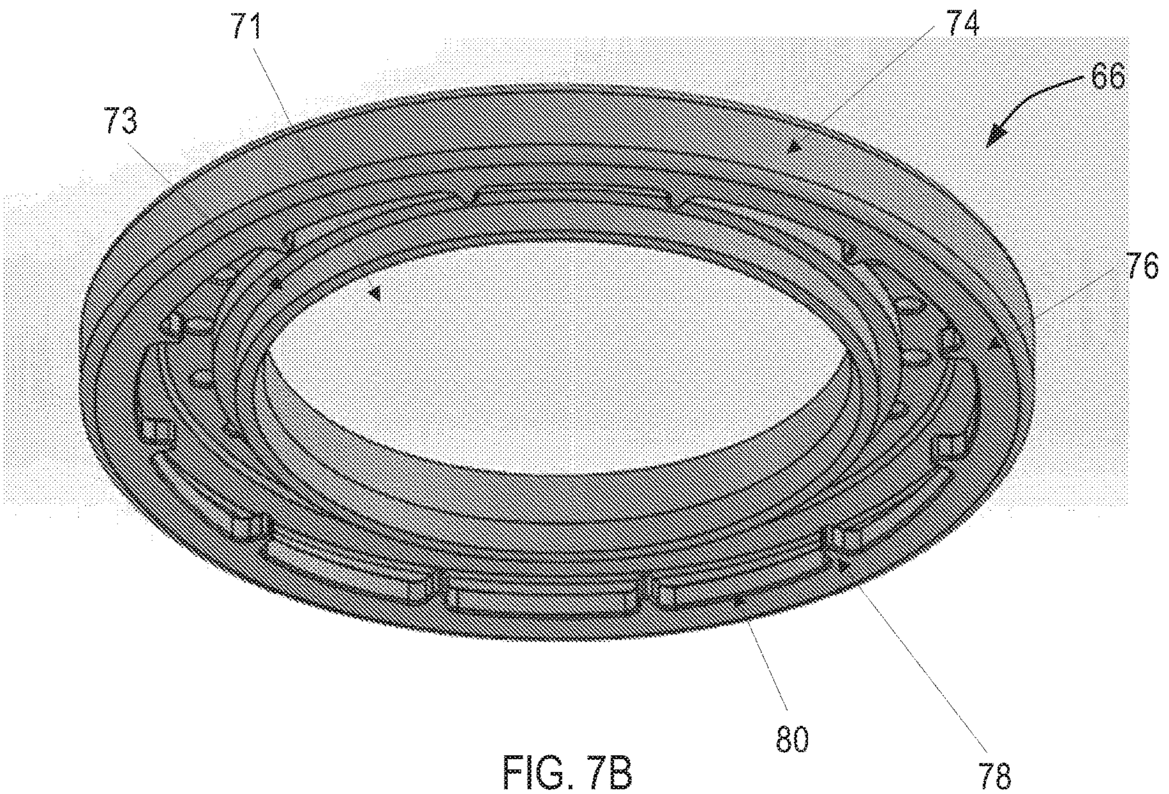

Referring now to FIGS. 7A and 7B, sewing ring 66 is described. Sewing ring 66 has opening 71 sized and shaped to receive inflow cannula 64 of blood pump 62. Sewing ring 66 includes upper planar portion 72 extending circumferentially forming opening 71, inner vertical portion 73 extending downward from the inner edge of planar portion 72 adjacent opening 71 of sewing ring 66, outer vertical portion 74 extending downward from the outer edge of planar portion 72 of sewing ring 66, and lower planar portion 76 extending from the lower edge of vertical portion 74 radially inward toward the longitudinal axis of sewing ring 66. Lower planar portion 76 may include a plurality of protrusions 78 circumferentially along an inner edge of planar portion 76, opposite from the edge of planar portion 76 coupled to vertical portion 74 of sewing ring 66. Plurality of protrusions 78 are separated by gaps 80, gaps 80 sized and shaped to receive the hook portion of locking element 70 as described in further detail below.

Figure 8:
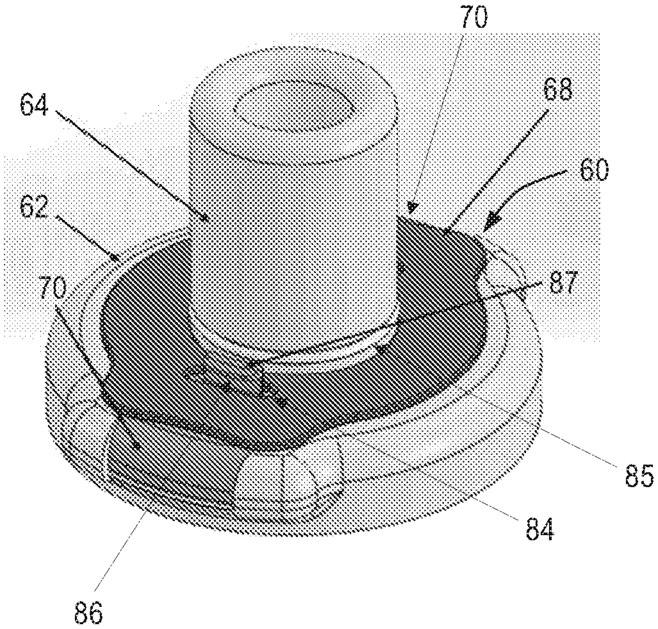
FIG. 8 illustrates the locking mechanism of FIG. 6 without the sewing ring.

As illustrated in FIG. 8, the housing of blood pump 62 may include ring 85 made of, e.g., rubber, disposed circumferentially about the external surface of inflow cannula 64. Accordingly, inflow cannula 64 may include a groove disposed circumferentially about the external surface of inflow cannula 64, the groove sized and shaped to receive ring 85 to form an impermeable seal against vertical portion 73 of sewing ring 66.

In addition, hood 68 includes opening 84 for receiving hook portion 86 of locking element 70. As illustrated in FIG. 8, locking mechanism 60 includes two locking elements 70, each having hook portion 86. Hook portion 86 of locking element 70 has a width selected to permit hook portion 76 to be received through gaps 80 of sewing ring 66. The upper surface of hook portion 86 may have sloped surface 87 such that as hook portion 86 is brought into contact with the lower surface of sewing ring 66, hook portion 76 moves radially inward toward the longitudinal axis of blood pump 62. Locking element 70 may include a button portion designed to be pushed radially inward toward the longitudinal axis of blood pump 62, thereby causing hook portion 76 to move from a closed state radially inward toward the longitudinal axis of blood pump 62 to an open state. In the open state, hook portion 76 may be received through gaps 80 of sewing ring 66. Upon release of the button portion of locking element 70, hook portion 76 returns to its initial position and is sandwiched between upper planar portion 72 and lower planar portion 76 of sewing ring 66, thus preventing translational and rotational movement of sewing ring 66 relative to locking element 70. As described in further detail below, locking element 70 may be bias toward the closed state such that after locking element 70 is moved to the open state to receive sewing ring 66, locking element 70 may automatically return to the closed state upon release of locking element 70.

Figure 9:
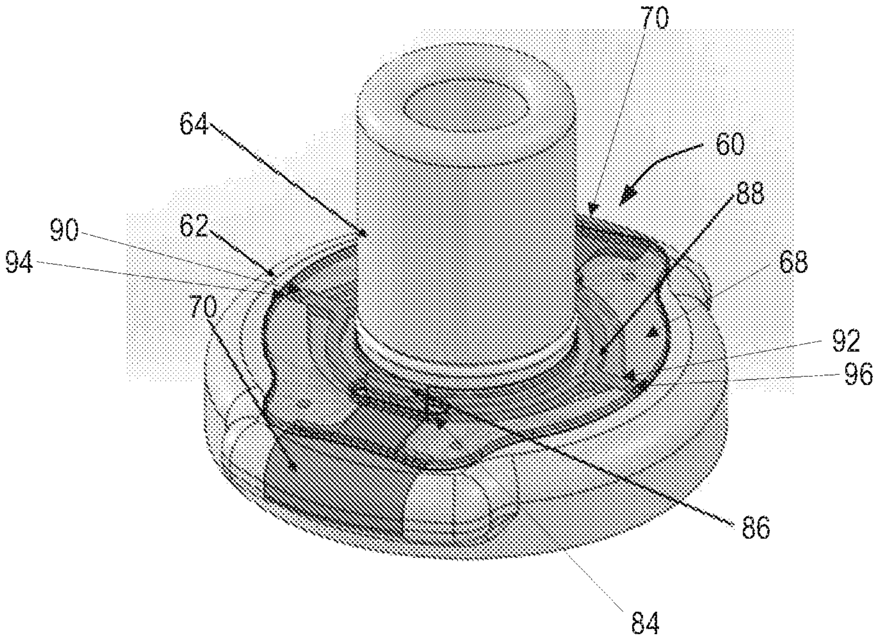
FIG. 9 illustrates the internal components of the locking mechanism of FIG. 8.

As illustrated in FIG. 9, locking mechanism 60 includes spring element 88 disposed on the upper surface of blood pump 62. Spring element 88 has first end 90 and second end 92, both sized and shaped to fit moveably within grooves 94 and 96, respectively. Grooves 94 and 96 are each positioned 45 degrees from locking element 70 along the upper surface of blood pump 62. In addition, spring element 88 has a circular shape and abuts hook portion 86 of locking 70 such that as locking element 70 moves from the closed state to the open state, spring element 88 compressed into a more oval shape. As spring element 88 compresses, first and second ends 90 and 92 move radially outward from the longitudinal axis of blood pump 62 within grooves 94 and 96, respectively. Upon release of locking element 70, spring element 88 returns to a relaxed state, and thus, pushes against locking element 70 in a radially outward direction to return locking element 70 the closed state.

Figure 10A:
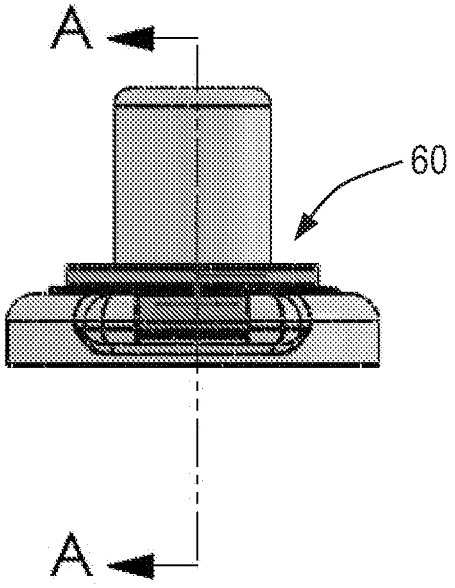
FIG. 10A illustrates a side view of the locking mechanism of FIG. 6, and FIGS. 10B and 10C illustrate a cross-sectional view of the locking mechanism of FIG. 10A.
Figure 10B:
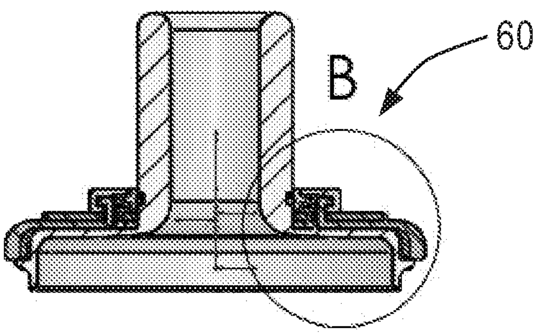
Figure 10C:
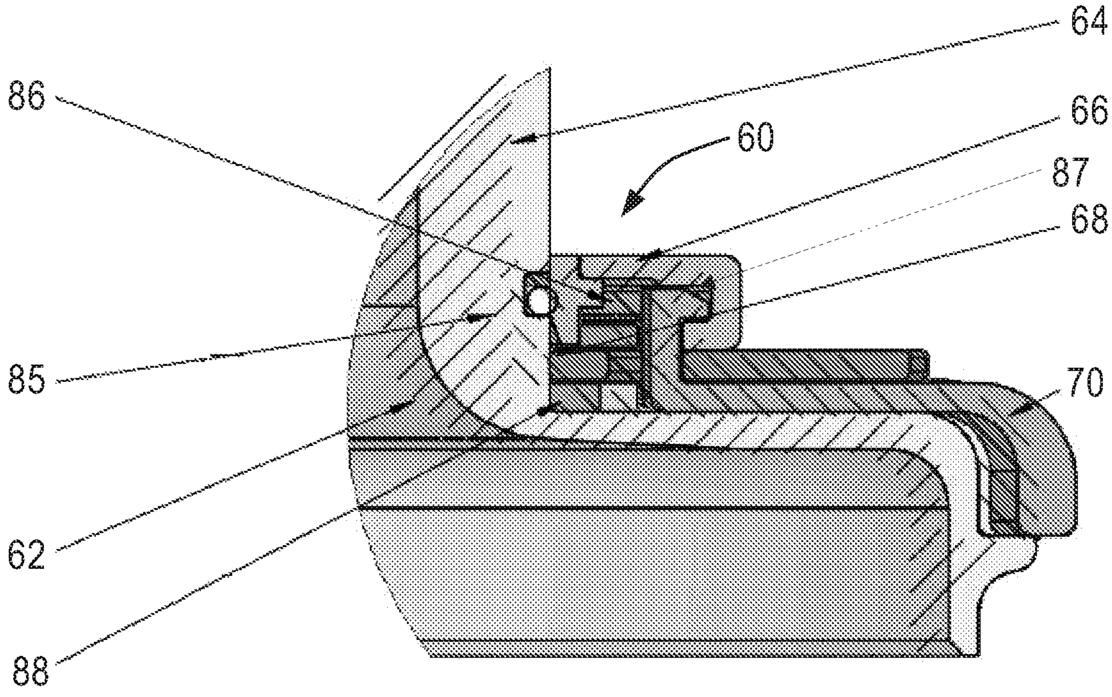

FIG. 10A illustrates a side view of locking mechanism 60 coupled to the housing of blood pump 62, and FIG. 10B illustrates a cross-sectional view of locking mechanism 60 coupled to the housing of blood pump 62 along line A-A of FIG. 10A. FIG. 10C illustrates an exploded view of circle B of FIG. 10B.

Figure 11:
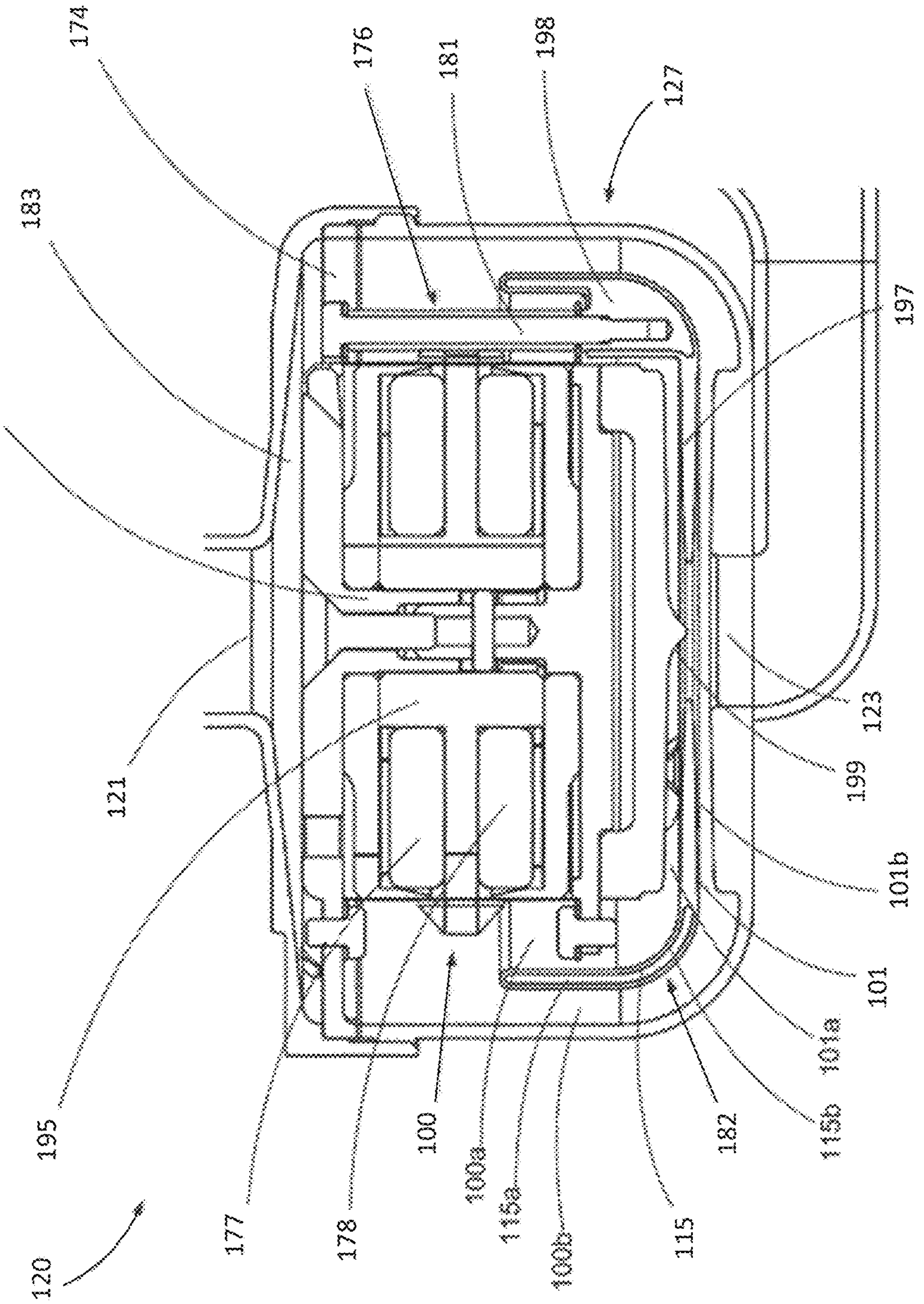
FIG. 11 is a cross-sectional view of an exemplary embodiment of an implantable pump of the present invention.

Referring now to FIG. 11, an exemplary embodiment of a blood pump (e.g., implantable pump) used in the present invention is illustrated. Implantable pump 120 may be the same as or similar to blood pump 12 of FIG. 1. As is illustrated in FIG. 11, the pump assembly is configured to fit within pump housing 127. To fix the pump assembly within pump housing 127, the pump assembly may include a fixation ring which may extend from and around stator assembly 172, and may be captured between an upper housing portion and a lower housing portion when the housing portions are assembled. In this manner, stator assembly 172 may be suspended within the pump housing in close-fitting relation to the interior walls of the pump housing. As shown in FIG. 11, stator assembly 172 may be suspended within, and prevented from moving within, pump housing 127. Pump housing 127 preferably is sized and configured to conform to the pump assembly such that, stator assembly 172 does not contact the interior of the pump housing at any location other than at the fixation ring.

Implantable pump 120 may include skirt 115 coupled to membrane 197. Skirt illustratively includes first portion 115 and second portion 115*b*. First portion 115*a* of skirt 115 extends upward within delivery channel 100 toward inlet 121 in a first direction, e.g., parallel to the longitudinal axis of stator assembly 172 and/or to the central axis of pump housing 127. Second portion 115*b* of skirt 115 curves toward outlet 123 such that second portion 115*b* is coupled to membrane 197 so that membrane 197 is oriented in a second direction, e.g., perpendicular to first portion 115*a* of skirt 115. For example, skirt 115 may have a J-shaped cross-section, such that first portion 115*a* forms a cylindrical-shaped ring about stator assembly 172 and second portion 115*b* has a predetermined radius of curvature which allows blood to flow smoothly from delivery channel 100 across skirt 115 to the outer edge of membrane 197 and into flow channel 101, while reducing stagnation of blood flow. Skirt 115 breaks flow recirculation of blood within delivery channel 100 and improves hydraulic power generated for a given frequency while minimizing blood damage. In addition, the J-shape of skirt 115 around stator assembly 172 is significantly more stiff than a planar rigid membrane ring, thereby reducing flexing and fatigue, as well as drag as the blood moves across membrane 197.

Skirt 115 exhibits rigid properties under typical forces experienced during the full range of operation of the present invention and may be made of a biocompatible metal, e.g., titanium. Skirt 115 may be impermeable such that blood cannot flow through skirt 115. Post reception sites 198 may be formed into skirt 115 to engage membrane assembly 182 with posts 181. Alternatively, posts 181 may be attached to skirt 115 in any other way which directly translates the motion of magnetic ring assembly 176 to skirt 115.

As magnetic ring assembly 176 moves up and down, the movement is rigidly translated by posts 181 to J-shape of skirt 115 of membrane assembly 182. Given the rigidity of the posts, when magnetic ring assembly 176 travels a certain distance upward or downward, membrane assembly 182 may travel the same distance. For example, when magnetic ring assembly 176 travels 2 mm from a position near first electromagnetic coil 177 to a position near second electromagnetic coil 178, membrane assembly 182 may also travel 2 mm in the same direction. Similarly, the frequency at which magnetic ring assembly 176 traverses the space between the first and second electromagnetic coils may be the same frequency at which membrane assembly 182 travels the same distance.

Skirt 115 may be affixed to membrane 197 and hold membrane 197 in tension. Membrane 197 may be molded directly onto skirt 115 or may be affixed to skirt 115 in any way that holds membrane 197 uniformly in tension along its circumference. For example, skirt 115 may be coated with the same material used to form membrane 197 and the coating on skirt 115 may be integrally formed with membrane 197.

Blood may enter implantable pump 120 from the left ventricle through inlet cannula (e.g., inflow cannula) and flow downward along the pump assembly into delivery channel 100. As the blood moves down tapered section 183 it is directed through gap 174 and into a vertical portion of delivery channel 100 in the area between pump housing 127 and actuator assembly 195. As shown in FIG. 11, skirt 115 divides delivery channel 100 into upper delivery channel 100*a* and lower delivery channel 100*b* such that blood flow through delivery channel 100 is divided into flow channel 101*a* via upper delivery channel 100*a* and flow channel 101*b* via lower delivery channel 100*b*, wherein flow channels 101*a* and 101*b* are separated by membrane 197. As will be understood by one of ordinary skill in the art, the volume of blood flow through each of delivery channels 100*a* and 100*b* may depend on the diameter of first portion 115*a* of skirt 115. For example, the larger the diameter of first portion 115*a* of skirt 115, the larger the volume of delivery channel 100*a* and the smaller the volume of delivery channel 100*b*. The ratio of the volume of delivery channel 100*a* to the volume of delivery channel 100*b* may be, for example, 1:1, 1:2, 1:3, 1:4, 2:1, 3:1, 4:1, etc., depending on the amount of desired blood flow on each surface of membrane 197.

By directing blood from inlet cannula 121 across skirt 115 within delivery channel 100, blood flow is divided into delivery channel 100*a* and 100*b* and to flow channels 101*a* and 101*b*, respectively, such that blood flows across the upper and lower surfaces of membrane 197 of membrane assembly 182. For example, as shown in FIG. 16A, blood flow through a pump having a planar rigid membrane ring spaced apart a relatively small distance from the pump housing may allow unrestricted blood flow across the upper surface of the flexible membrane while restricting blood flow across the lower surface of the flexible membrane. Whereas, as depicted in FIG. 16B, blood flow through a pump having a J-shaped skirt may be distributed across both the upper and lower sides of the flexible membrane at a desired ratio.

By actuating electromagnetic coils 177 and 178, membrane 197 may be undulated within flow channels 101*a* and 101*b* to induce wavelike formations in membrane 197 that move from the edge of membrane 197 towards circular aperture 199. Accordingly, when blood is delivered to membrane assembly 182 from delivery channel 100, it may be propelled radially along both the upper and lower surfaces of membrane 197 towards circular aperture 199, and from there out of outlet 123 and outflow cannula. The distribution of blood flow across the upper and lower surfaces of membrane 197 reduces recirculation of blood within delivery channel 101, and reduces repeated exposure of blood to high shear stress areas, which results in remarkably improved hydraulic performance of implantable pump.

Figure 12:
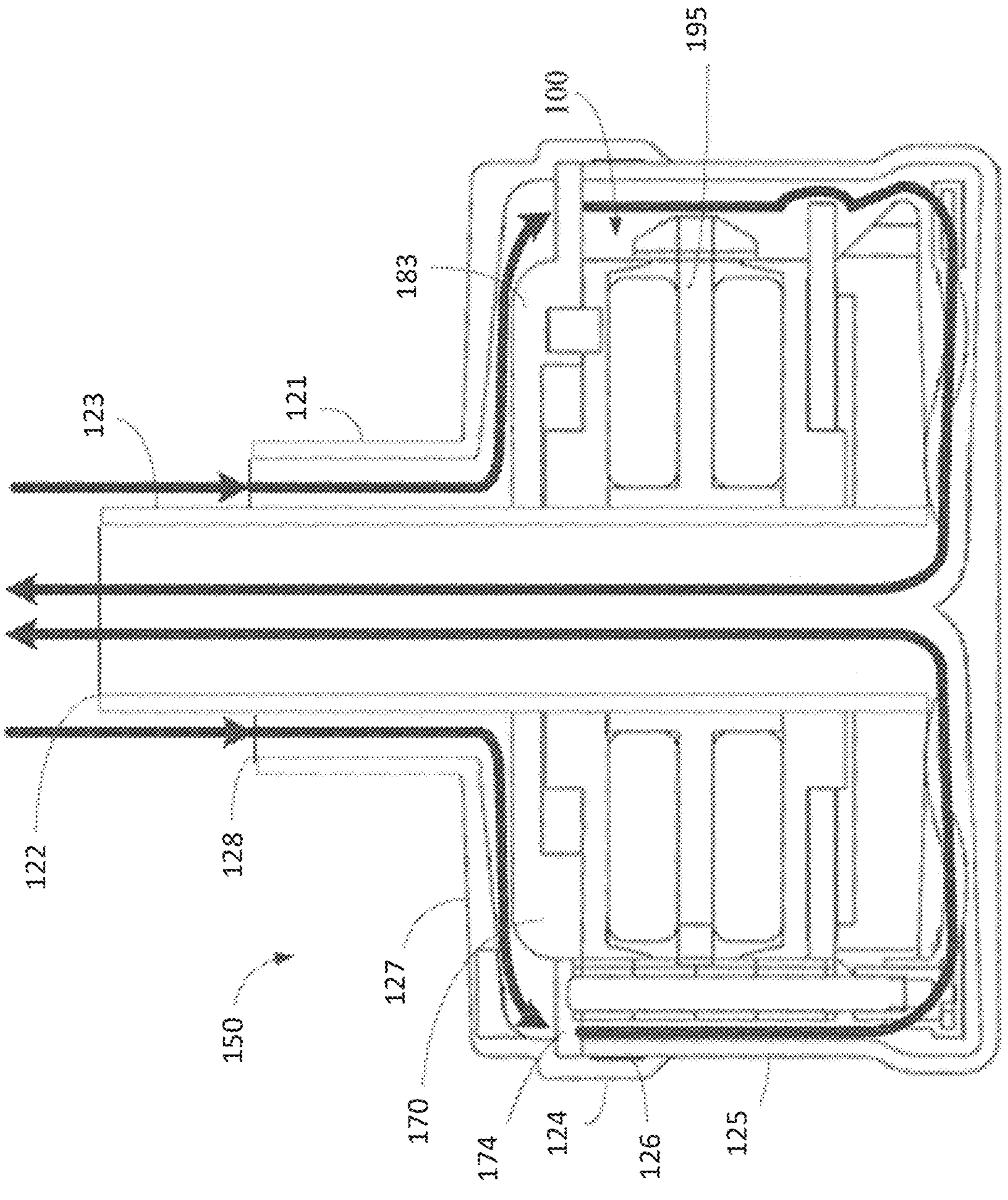
FIG. 12 is a cross-sectional view of an another exemplary implantable pump of the present invention.

Referring to FIG. 12, a sectional view of implantable pump 150 is shown. The pump illustrated in FIG. 12 is a vibrating membrane pump. However, it is understood that implantable pump 150 may employ any type of pump well-suited for use as a left ventricular assist device and sized and configured to fit within pump housing 127. As is illustrated in FIG. 12, pump housing 127 includes upper housing portion 124 joined to lower housing portion 125 along interface 126. As also illustrated in FIG. 12, pump housing and the pump are configured to orient inflow cannula 121 and outflow cannula 123 in a coaxial orientation. Inflow cannula 121 may be separate and distinct from upper housing portion 124 or may alternatively be incorporated into the same component, as is shown in FIG. 12. Outflow cannula 123 may be incorporated into pump assembly 170, as is shown in FIG. 12. For example, outflow cannula may be affixed to or may extend from a stator of a vibrating membrane pump. Alternatively, outflow cannula 123 may be coupled to inflow cannula 121 or to upper housing portion 124 in a manner that permits blood to flow between inflow cannula 121 and outflow cannula 123. For example, inflow cannula 121 may suspend outflow cannula 123 in a coaxial manner using struts that extend out from inflow cannula 121 and permit blood to flow between inflow cannula 121 and outflow cannula 123.

Inflow cannula 121 and outflow cannula 123 are configured to be in fluid communication with one another such that blood enters an inlet 128 of inflow cannula 121, travels through annular inflow cannula 121 and fills up the pump. The pump increases flow and pressure and directs blood from the pump into outflow cannula 123 and ultimately out outlet 122. In this manner, blood may enter and exit from the same general area such as the same heart chamber. As outflow cannula 123 is configured to extend beyond inflow cannula 121, the blood that exits outflow cannula 123 is not likely to enter inflow cannula 121.

While various illustrative embodiments of the invention are described above, it will be apparent to one skilled in the art that various changes and modifications may be made herein without departing from the invention. It will further be appreciated that the devices described herein may be implanted in other positions in the heart. The appended claims are intended to cover all such changes and modifications that fall within the true spirit and scope of the invention.

What is claimed:

1. A system comprising:

a blood pump comprising an inlet and an outlet as well as an inflow cannula extending from the inlet and an outflow cannula extending from the outlet, the blood pump configured to pump blood from the inlet to the outlet, the inlet and the outlet aligned coaxially and configured to direct blood flow in parallel directions to one another, the inflow cannula comprising at least one first groove configured to receive a sealing ring; and an apparatus for coupling the blood pump to a patient's heart, the apparatus comprising:

a sewing ring configured to be sutured to the patient's heart;

a vertical portion forming an annular shape and coupled to the sewing ring, the vertical portion comprising an opening sized and shaped to receive the inflow cannula of the blood pump and to interface with the sealing ring to form an impermeable seal between the inflow cannula of the blood pump and the vertical portion;

a locking mechanism configured to be coupled to a housing of the blood pump and transitionable between a closed state and an open state, the locking mechanism comprising a biased structure, the locking mechanism configured to prevent translational and rotational movement of the locking mechanism relative to the housing of the blood pump when the locking mechanism is in the closed position, wherein the biased structure is configured to bias the locking mechanism to transition between the open state and the closed state, and wherein the biased structure is configured to fit moveably within at least one second groove of the locking mechanism as the biased structure transitions between the open state and the closed state.

2. The system of claim 1, wherein the locking mechanism comprises a plurality of horizontal crenellations disposed along a circumferential opening of the locking mechanism, the plurality of horizontal crenellations of the locking device separated by a plurality of gaps sized and shaped to receive a plurality of horizontal crenellations disposed adjacent the opening of the sewing ring when the locking mechanism is in the open state.

3. The system of claim 2, wherein in the closed state, the plurality of horizontal crenellations of the locking mechanism are aligned with the horizontal crenellations of the sewing ring to prevent translational movement of the housing of the blood pump relative to the sewing ring.

4. The system of claim 2, wherein the housing of the blood pump comprises a plurality of vertical crenellations, the plurality of vertical crenellations of the housing of the blood pump configured to receive corresponding indentations of the sewing ring to prevent rotational movement of the housing of the blood pump relative to the sewing ring.

5. The system of claim 2, wherein the biased structure comprises a first end and a second end, the biased structure disposed circumferentially about a longitudinal axis of the blood pump between the first and second ends, the first end of the biased structure coupled to the housing of the blood pump, the second end of the biased structure coupled to the locking mechanism via a locking pin, the locking pin moveable within a third groove on the housing of the blood pump to permit movement of the second end of the biased structure.

6. The system of claim 5, wherein the locking mechanism is configured to rotate about a longitudinal axis of the housing of the blood pump to transition from the closed state to the open state, and wherein rotation of the locking mechanism causes the second end of the biased structure to move from a first position in the closed state to a second position toward the first end in the open state, thereby compressing the biased structure in the open state.

7. The system of claim 2, wherein the locking mechanism comprises a plurality of brackets configured to engage with the housing of the blood pump, the plurality of brackets each comprising a third groove sized and shaped to accept one or more guide rails disposed on a surface of the housing of the blood pump such that the plurality of brackets moves along the one or more guide rails as the locking mechanism transitions between the closed state and the open state.

8. The system of claim 2, wherein the housing of the blood pump comprises a stop, the stop configured to limit rotation of the locking mechanism relative to the housing of the blood pump, and wherein a notch of the locking mechanism engages the stop in the open state.

9. An apparatus for coupling a blood pump to a patient's heart, the apparatus comprising:

a sewing ring configured to be sutured to the patient's heart;

a vertical portion forming an annular shape and coupled to the sewing ring, the vertical portion comprising an opening sized and shaped to receive an inflow cannula of the blood pump and to interface with a sealing ring received in at least one first groove of the inflow cannula to form an impermeable seal between the inflow cannula of the blood pump and the vertical portion; and a locking mechanism configured to be coupled to a housing of the blood pump and transitionable between a closed state and an open state, the locking mechanism comprising a biased structure configured to contact the blood pump, the locking mechanism configured to prevent translational and rotational movement of the locking mechanism relative to the housing of the blood pump when the locking mechanism is in the closed position, wherein the biased structure is configured to bias the locking mechanism to transition between the open state and the closed state, and wherein the biased structure is configured to fit moveably within at least one second groove of the locking mechanism as the biased structure transitions between the open state and the closed state.

* * * * *